US00PP15900P3

(12) United States Plant Patent
Peterson

(10) Patent No.: US PP15,900 P3
(45) Date of Patent: Aug. 2, 2005

(54) PAWPAW TREE NAMED 'LEVFIV'

(50) Latin Name: *Asimina triloba*
Varietal Denomination: Levfiv

(76) Inventor: Robert Neal Peterson, P.O. Box 1277, Franklin, WV (US) 26807

( * ) Notice: Subject to any disclaimer, the term of this patent is extended or adjusted under 35 U.S.C. 154(b) by 268 days.

(21) Appl. No.: 09/954,186

(22) Filed: Sep. 17, 2001

(65) Prior Publication Data

US 2003/0056254 P1 Mar. 20, 2003

(51) Int. Cl.[7] ..... A01H 5/00
(52) U.S. Cl. ..... Plt./156
(58) Field of Search ..... Plt./156

*Primary Examiner*—Bruce R. Campell
*Assistant Examiner*—Susan B. McCormick

(57) ABSTRACT

Disclosed herein is a new and distinct variety of pawpaw tree, which has been given the name 'Levfiv.' This variety is distinguished by its all-around excellent fruit quality consisting of large, firm, fleshy, thick skinned fruits with an unusually low seed-to-fruit ratio and an excellent flavor. This variety possess the fleshiest and firmest fruit in pawpaws found to date. The texture is firm and smooth. The number of fruit per cluster is low, often in singles, which simplifies harvesting. The fruit possesses a color break at picking stage which is a major advantage in harvesting the fruit. The fruit firmness plus the thick skin will help in shipping and handling. This variety is one of three varieties newly identified as having potential to establish a commercial pawpaw industry.

8 Drawing Sheets

BACKGROUND OF THE INVENTION

The present invention relates to a new and distinct and superior variety of the pawpaw which is of interest for its fruit.

The species—*Asimina triloba* (L.) Dunal—is the largest native edible fruit of North America, a member of the Annonaceae family, and thus a relative of the cherimoya, sweetsop, guanabana and custard apple (*Annona cherimola, A. squamosa, A. muricata* and *A. reticulata*), all of which are popular fruits that are widely cultivated in tropical and subtropical regions of the world, including southern Florida and southern California. The pawpaw is the only truly temperate member of the Annonaceae, being indigenous to a region stretching from the Great Lakes to the Gulf Coastal Plain and from the Chesapeake Bay to the Great Plains.

Currently, the pawpaw is considered to be semi-domesticated. Native Americans casually cultivated the tree, as did the white settlers who displaced them. The selection, propagation and naming of pawpaw varieties from the wild has been practiced for more than a century, and the backyard cultivation of pawpaws for personal use is not uncommon in Appalachia and parts of the Midwest. Numerous unregistered, unpatented varieties are available in the mail-order nursery trade.

Commercial cultivation of pawpaw has not developed, however. The fruit is fragile and highly perishable which makes transport difficult. And scientific attention towards improving the fruit, its culture and its postharvest handling has been neglected until recently. The lack of high quality cultivars that meet the requirements of producers and consumers is the foremost reason that commercial cultivation has not been undertaken.

The present invention, named 'Levfiv,' is one of three new and distinct varieties of pawpaw each of which represents a great improvement over existing pawpaw varieties because of higher yields, superior flavor, fewer seeds and firmer flesh. The other two varieties are 'Aidfievate', which is the subject of co-pending application Ser. No. 09/954,140, and 'Wansevwan', which is the subject of co-pending application Ser. No. 09/954,536. These varieties possess the minimum overall qualities required for the development of a commercial pawpaw industry. The primary use of this pawpaw variety will be for fresh eating as a dessert fruit. Secondary use will be in processed products such as ice cream, yogurt, juice and cosmetics. Of the three, the variety 'Levfiv' is outstanding for combining large fruit size with high firmness, great fleshiness and good flavor.

ORIGIN

The variety 'Levfiv' was developed by R. Neal Peterson as the result of a breeding project to improve the pawpaw, which he began in 1980. The project was conducted during a period when Peterson was employed as an economist with the Economic Research Service of the United States Department of Agriculture in Washington, D.C. However, because Peterson was not employed in any capacity as a horticulturist or other researcher in the biological sciences, and no Department of Agriculture plant stock, facilities or information was used, the United States government has no interest in the rights to the claimed variety.

The germplasm for Peterson's breeding project came principally from the surviving remnants of five historic collections of pawpaw dating to the early twentieth century that were the work of the most prominent pawpaw collectors and breeders of the time, and whose named material was no longer propagated or otherwise available. In 1982 germ plasm [open-pollinated seed] was collected from these remnants and included with open-pollinated seed from named cultivars, which became the germ plasm for his own breeding and selection work.

In 1983 the seed was germinated and in the following spring 808 accessions were planted at the University of Maryland experiment station, the Wye Research & Education Center, Queenstown, Md. Since then, the orchard has been supervised by the inventor, with basic staff support from the university. Basic tasks such as fertilizing, spraying and mowing were conducted by the station staff. The inventor pruned, weeded, and collected data on growth rates, flowering, fruit set, yields, cluster size, fruit size and fruit quality, including data from taste panels which he organized.

In 1991, the inventor analyzed four years of data, and concluded in identifying eleven trees as superior for further study. Nine of these are involved in regional variety trials around the country and have been termed advanced numbered selections. After nine additional years of observation, the original nine were narrowed to three that were consistently of the highest quality. One of these bears the accession number PPF 11-5 and is the variety that is the subject of this application. The original tree PPF 11-5 is 18 years old. This new variety, named 'Levfiv,' originated as an open-pollinated seedling from a pawpaw tree on the grounds of the Blandy Experimental Farm, Boyce, Va., which tree was given the label BEF-53 by the inventor. Pawpaw BEF-53 is believed to have been a cataloged accession of the Blandy Experimental Farm's collection of *Asimina triloba* (circa 1922–1955) although records to support this contention are now missing. To our knowledge BEF-53 has never been asexually propagated.

ASEXUAL REPRODUCTION OF THE VARIETY

In 1994, the inventor began topworking the Wye orchard to his eleven advanced numbered selections, plus named varieties. Topworking was accomplished using bark-inlay grafting and chip-budding. Grafting of 'Levfiv' was easy by either method, and gave a high percentage of success. Replicates of 'Levfiv' now number more than 20 at the Wye, having been propagated through successive cycles of grafting over seven years. The rootstock for these grafts were mature seedling pawpaw trees growing in the orchard, and were a portion of the original accessions from 1983, described previously. Four grafted trees of 'Levfiv' have now been in bearing since 1997 and demonstrate that asexual reproduction of this new and distinct variety preserves the desirable characteristics of the variety and establishes and stably transmits those characteristics through successive propagation at the Queenstown location.

SUMMARY OF THE VARIETY

'Levfiv' possesses exceptional fruit quality, combining as it does in a single variety large size, firm texture, very few seeds and excellent flavor. The fruit is extremely large, on average 300 gm for well-pollinated fruit, and may exceed 450 gm. The cluster size varies, but is commonly one, two or three fruited. Fruit shape is broadly ellipsoidal to nearly spherical. The skin is thicker and tougher than is typical for the species. Skin color is pale yellow-green and slightly glaucous, and is uniformly speckled with minute black dots the size of pin pricks. The fruit normally exhibits a color-break at the stage for picking, which is visible as a brownish collar around the neck of the fruit. This color break is reliable and can be easily discerned with practice. The composition of the fruit is extremely fleshy, with many fewer seeds relative to fruit weight than is typical of pawpaw. Seed size is large. The aroma of the fruit before and after cutting is pleasant and mild. The flavor is excellent, though not as good as 'Wansevwan'—mild, sweet, free of bitterness or astringency, with a pleasant aftertaste. The pungent asiminous component that is uniquely pawpaw and that many people find objectionable is very low. The flesh is very firm and very smooth with a consistency resembling 'Haas' avocado, and produces a very pleasant mouth-feel. It has no detectable fiber or grit. The ripening period at Queenstown has been mid to late season, September 12 to 27, more or less, depending on the degree of heat in the preceding months.

Several non-fruit characters of 'Levfiv' also serve to distinguish it from other pawpaws. For the most part, leaf characters (size, color, shape and aspect) are typical of pawpaw. Unlike typical pawpaw, however, the upper surface of the leaf is distinctly rugose. This rugoseness, though not pronounced, is evident in both young and mature leaves, and is a trait unique to 'Levfiv' plus a few other progeny from the same mother tree, BEF-53. The petioles are shorter than usual for the species. The branching habit is widely spaced with wide crotch angles normally. Flower measurements when taken as a whole may identify 'Levfiv' though perhaps not uniquely. Its flowers are medium in size, outer petals orbicular, and are notable for having petals that are not as recurved and flaring in the male stage as is typical for the species. For exact data, see the detailed description and accompanying photographs.

This variety is susceptible to *Talponia plummeriana*, the pawpaw peduncle moth, is susceptible to *Eurytides marcellus*, the zebra swallowtail butterfly, and is believed to be susceptible to pawpaw decline disease, the same in all cases as the species. This variety does not require pruning except to control ultimate tree size. It responds well to pruning, forming a broadly spreading tree of globular shape with normally wide crotch angles. Pruning has an invigorating effect that stimulates growth and fruit bearing. Corrective pruning is minimal. Tree vigor is less than most pawpaws and this variety may need to be grafted onto more vigorous rootstocks to promote good growth and heavier bearing. Fruit yields are moderate, somewhat less than 'Wansevwan.'

BRIEF DESCRIPTION OF THE DRAWING

In the accompanying drawings, leaves, flowers, fruits and seeds are shown in color that is as nearly true as is reasonably possible to make in color photographs of this nature. The deep maroon hues of the flowers are the most difficult for photoemulsions to render accurately.

BOTANICAL DESCRIPTION

Figure 1:
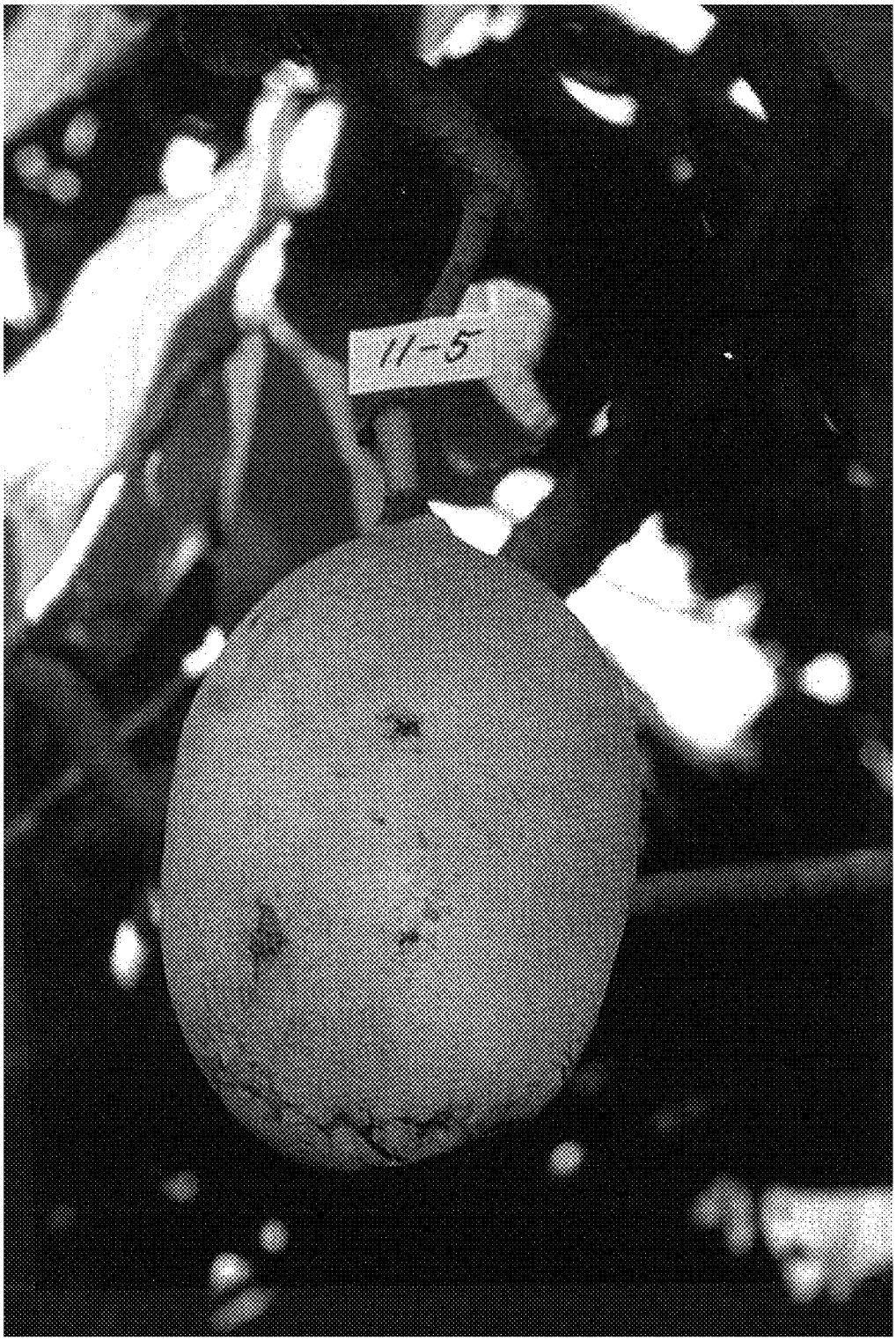
FIG. 1 Shows the fruit of the new variety, hanging on the tree.
Figure 2:
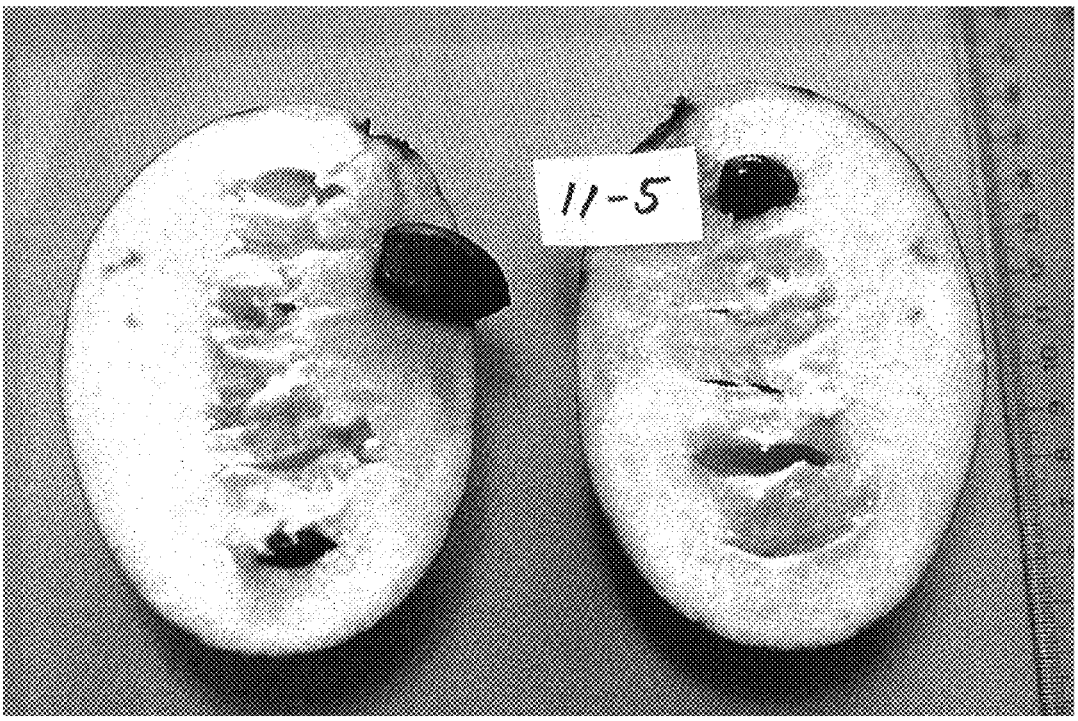
FIG. 2 Shows the fruit of the new variety in dissection, revealing the color, fleshiness and seeds.
Figure 3A:
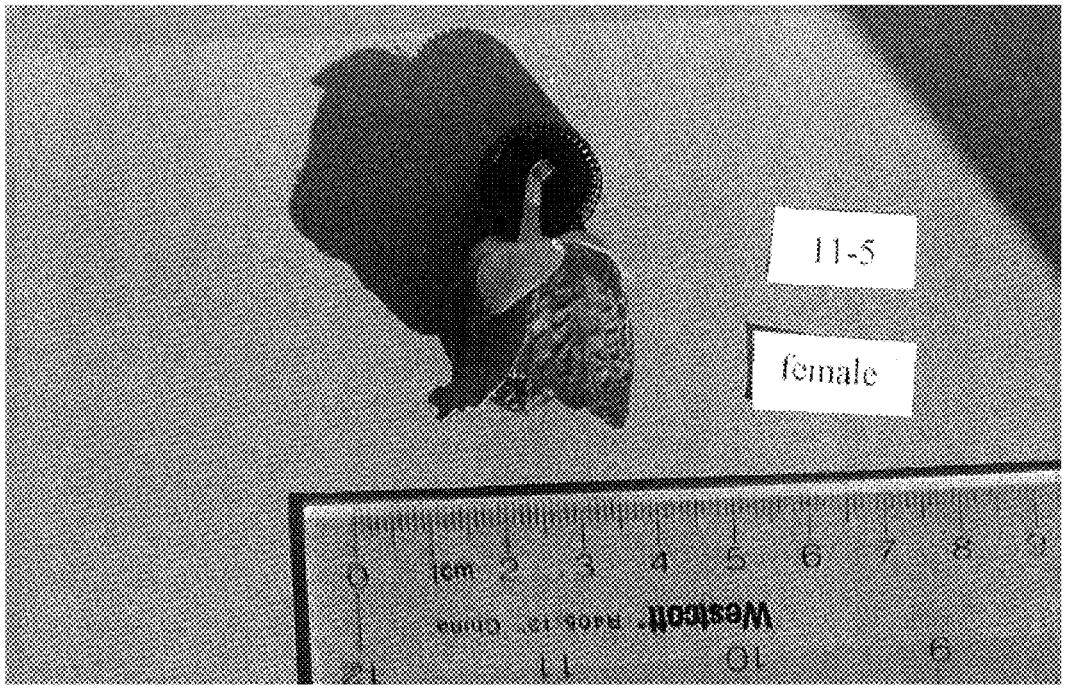
FIG. 3 Shows the flower of the new variety in the female stage, in profile and dissection.
Figure 3B:
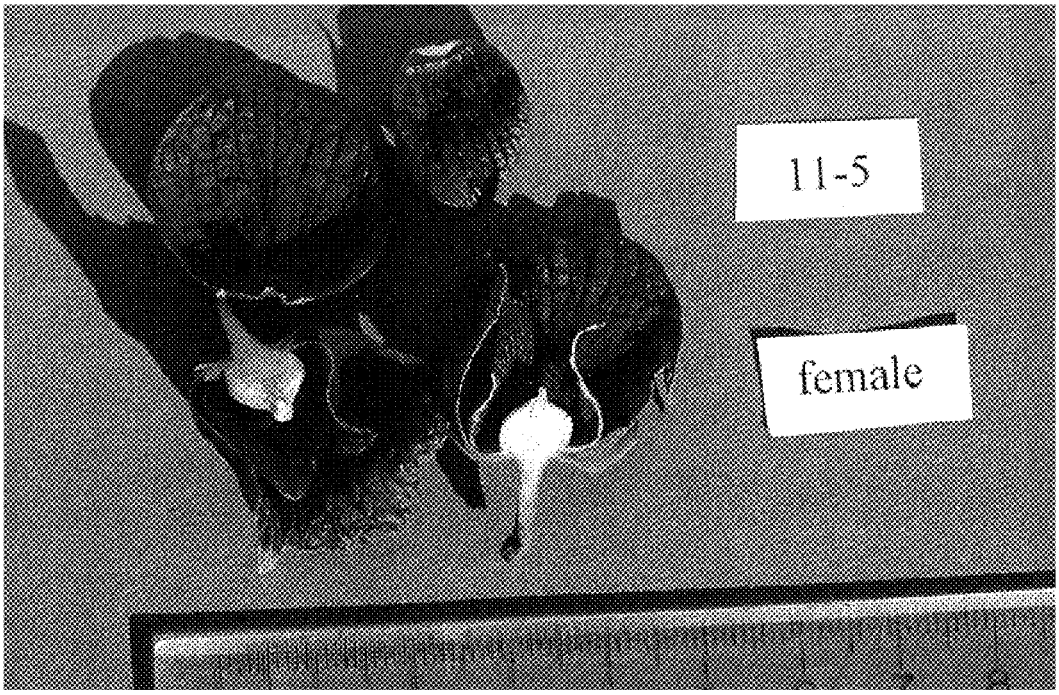
Figure 4A:
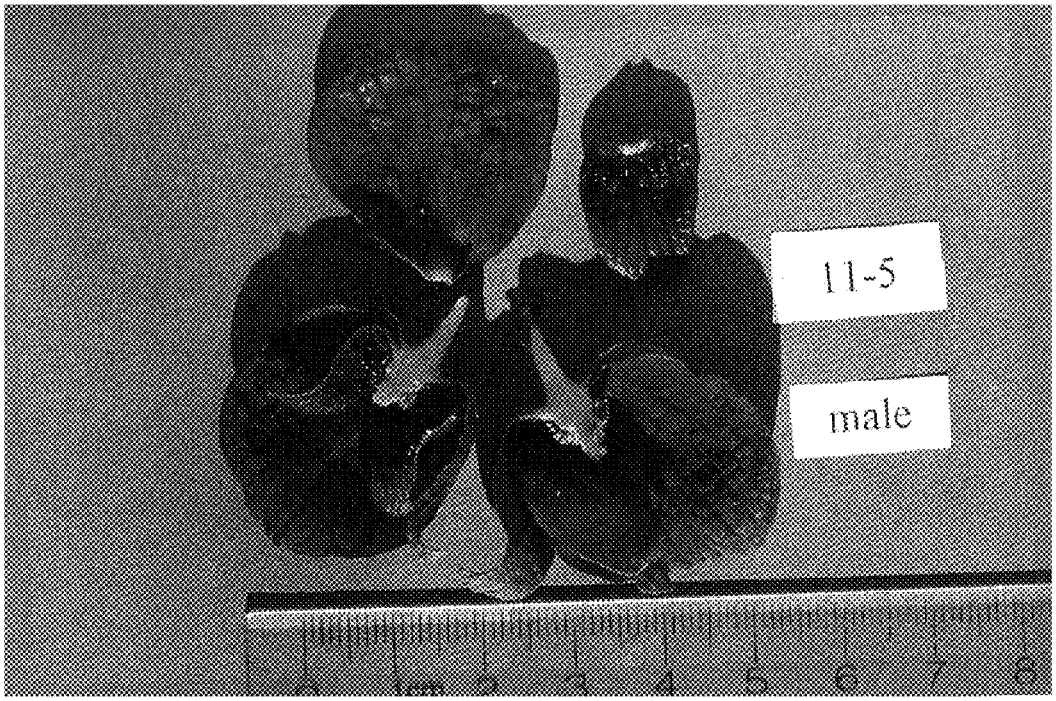
FIG. 4 Shows the flowers of the new variety in the male stage, in profile and dissection.
Figure 4B:
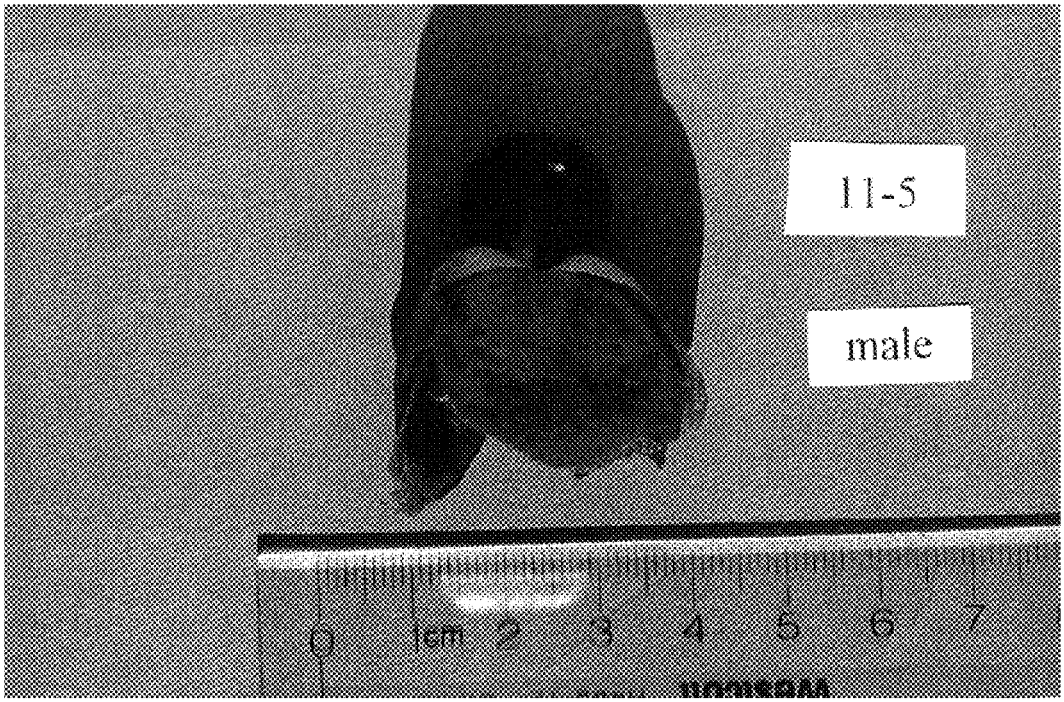
Figure 5:
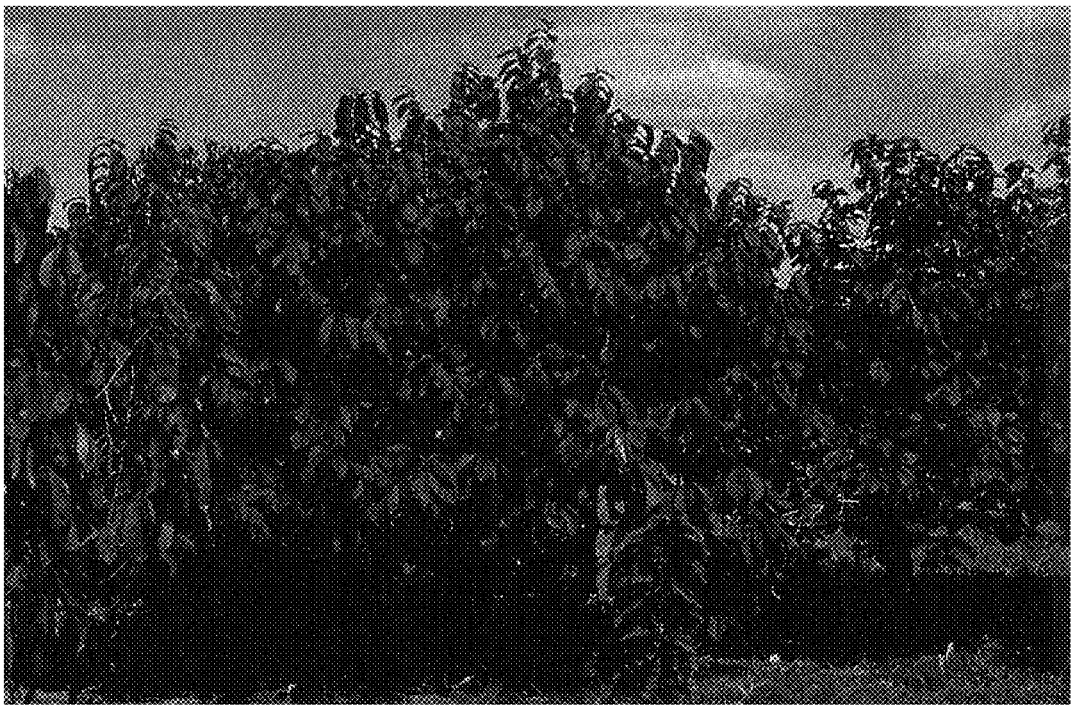
FIG. 5 Shows the habit of a pruned tree of the new variety.
Figure 6:
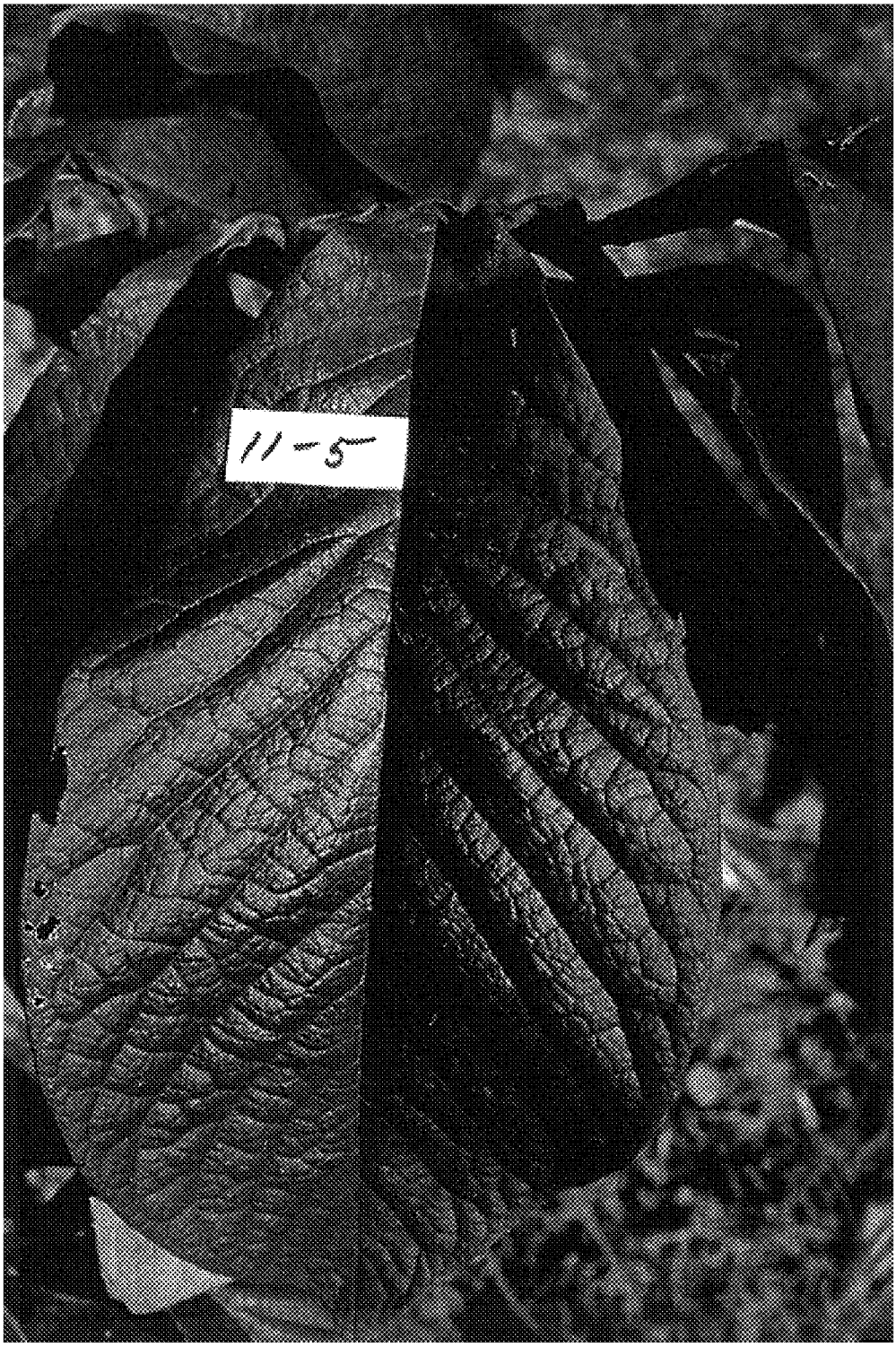
FIG. 6 Shows a close-up of the leaves of the new variety.

Because no variety of *Asimina triloba* has had application made to the Patent Office, we include a botanical description of the species drawn from two taxonomic authorities, C. S. Sargent and R. Kral.

Shrub or small tree 1.5–11 (~14) m tall from a stout, sometimes branched taproot, with a straight trunk seldom exceeding 30 cm in diameter; the bark of older trees gray-brown, shallowly furrowed, and marked with large ash-colored blotches; that of new shoots moderately to copiously dark brown-hairy toward the summit, aging smooth, gray-brown; winter vegetative buds naked, without stipules, acuminate and dark brown to rusty brown-hairy, 2–5 mm long, and tightly appressed against the stem; winter flower buds globose, dark brown-hairy, 2.5–5 mm in diameter; leaves membranaceous, oblong-obovate to oblanceolate, 15–30 cm long; apex acute to acuminate; base more or less gradually attenuate to the short (0.5–1 cm) petiole; margin flat or scarcely revolute; young surfaces sparsely appressed reddish-pubescent above; densely so beneath, becoming glabrous above and sparsely hairy on the veins beneath; flowers green initially, then turning brown to maroon to deep vinous red, 2–5 cm broad with a faintly fetid aroma, on densely dark brown-hairy, nodding peduncles 1–2.5 cm long which develop from the axils of the prominent leaf scars; calyx 8–12 mm long, of three triangular-deltoid sepals which are striate with brown hairs on the outside, glabrous within; outer petals 1.5–2.5 cm long, oblong-elliptic, with ascending bases and slightly to conspicuously recurved tips, copiously appressed-hairy along the veins outside, glabrous and impressed-veiny within; inner petals ⅓–½ the length of the outer, elliptic, saccate-based, recurved tipped, glabrate without, glabrous and impressed-veiny within, with a corrugated nectary zone usually of a lighter color; androecium globular, 0.5–1 cm broad, pale green at anthesis; gynoecium of 3–10 fusiform appressed-red-hairy carpels; fruits oblong-cylindric, 5–15 cm long, yellow-green to brownish when ripe, attached obliquely to the enlarged torus of the peduncle in clusters of variable number; seeds 1.5–2.5 cm long, brown to castaneous, shiny when mature, bean-shaped, somewhat laterally compressed, contained within an aril that is confluent with the pericarp from which the seed readily separates.

DETAILED DESCRIPTION OF THE INVENTION

Following is a detailed description of the new variety of pawpaw tree with color terminology in accordance with The Royal Horticulture Society (R.H.S.) Colour Chart (Ed. No. 2, 1986) except where general color terms of ordinary dictionary significance are used.

Tree:

*Size.*—Medium. 4.5 m on its own roots but taller on more vigorous rootstock.

*Vigor.*—Low to medium when grafted onto other rootstock. Approximately 42 cm growth on strong primary laterals under standard fertilization of 50 lbs of N per acre.

*Habit.*—Rounded with age, but taller than broad in the unpruned condition.

*Branching pattern.*—Spreading. Crotch angles wide. Branches widely spaced.

*Apical dominance.*—Medium.

*Trunk.*—Diameter 14.6 cm measured at 30 cm above ground level.

*Bark.*—Smooth with small raised horizontal lenticels, typical of the species. Color between R.H.S. Greyed-Green 197A and Grey 201B on both trunk and branches.

Leaf buds:

*Length.*—Axillary buds growing on branches of normal vigor, 3.8 mm average with a range of 3.2 to 4.5 mm. Buds growing on branches of high vigor larger, 5.9 mm average with a range of 4.5 to 7.4 mm.

Leaves:

*Shape.*—Oblanceolate with acuminate tip and attenuate to the base, as is typical for the species. Average ratio of width to length is 0.490.

*Size.*—Measurements are from mature leaves attached at midpoint of actively growing shoots of current season's growth. Average size is 13.5 cm wide, 27.5 cm long.

*Color.*—Upper surface varies from R.H.S. Green 139A to Yellow-Green 147A. Lower surface R.H.S. Yellow-Green 146A. Both colors typical for the species.

*Aspect.*—Drooping when grown in full sun, as is typical for the species.

*Margin.*—Entire.

*Texture.*—Upper surface slightly but distinctly rugose, very atypical for the species.

*Arrangement.*—Alternate opposite.

*Petiole.*—Color yellow-green similar to lower leaf surface. Average diameter 3.3 mm at the petiole midpoint. Length ranges from 10.0 to 12.9 mm with an average of 11.4 mm. NOTE: The structure of the leaf lamina is such, in the way that it tapers gradually to the petiole, that visual demarcation of the petiole terminus is imprecise and the resultant measurement of petiole length has a high margin of error. The measurements reported here are based on a tactile method that is more precise. By means of running the back of one's thumbnail down the midvein (on the underside of the leaf) towards the petiole one encounters a sudden change in curvature, diameter, and hardness. This point of change is the petiole terminus and is easy to detect and replicate.

Flower buds:

*Size.*—Length 4.8 mm average. Width 4.2 mm average.

*Appearance.*—Very dark brown, between R.H.S. Brown 200A and Black 202A. Surface densely pubescent, velvety.

Flower:

*Size.*—Medium to small. As the flower matures from female to male stage, the petals reflex, and therefore measured flower size is specific to flower stage, which data are presented below.

*Outer petals.*—Average of 26 mm wide, 28 mm long. Average ratio of width to length is 0.93.

*Inner petals.*—Average of 13 mm wide, 19 mm long. Average ratio of width to length is 0.67.

*Color.*—Maroon.

*Form of female stage flower.*—Slightly less closed than typical.

*Size of the female stage flower.*—Diameter 27 mm average.

*Nectary band of female stage flower.*—Reddish-maroon color, not as dark as surrounding inner petal.

*Form of male stage flower.*—Outer and inner petals recurved and only slightly more flaring than in the female stage, much less so than typical for pawpaw.

*Size of the male stage flower.*—Diameter 35 mm average.

*Nectary band of male stage flower.*—A deep maroon color, basically indistinguishable from the inner petal color.

*Peduncle.*—Short, average length 10 mm. Lightly pubescent with dark brown hairs.

Fruit:

*Dates of picking.*—Mid to late season, generally from September 12 to 27 at Queenstown, but dates can vary by more than a week depending on the degree of summer heat.

*Cluster size.*—Few fruited. One, two and three-fruited clusters are prevalent, and this small cluster size is atypical of pawpaw. Larger clusters occur, however, even exceeding five fruits. Within large clusters the fruit size typically varies considerably. High within-cluster variance of fruit size is common in pawpaw.

*Fruit shape.*—From broadly ellipsoidal to somewhat cylindrical with rounded ends. Shape varies considerably; but large well-formed fruit in a single-fruited cluster tend towards length-to-width-to-depth proportions of 100:73:70.

*Fruit size.*—Very large, 300 gm average for well-pollinated fruit. Much larger than typical pawpaw. Size varies from small (~42 gm) to very large (~500 gm), dependent on the number of fertilized seed present in the fruit. Lengths normally range 5.5–13.0 cm, widths 4.0–9.5 cm, and depths 3.8–9.0 cm.

*Suture.*—Fine green line, usually present.

*Abcission type.*—Primary mode is for fruit to abscise from the torus of the peduncle.

*Abscission scar.*—Large, 10.8 mm in diameter. A character of low variance.

*Peduncle.*—Length 18.7 mm on average, ranging from 16.0 to 21.5 mm. Diameter extremely variable, varying in proportion to the cluster fruit mass, as is typical of the species. However, in comparison to the range of peduncle sizes of pawpaw cultivars, and relative to the total cluster fruit weight, the diameter is thick. Peduncle pubescence dark brown, varies from dense to sparse, typically dense. The point of peduncle attachment to single-fruited clusters is near the central axis of the fruit, slightly offset to the dorsal side.

*Skin color.*—Under-ripe fruit pale green and glaucous, ranging from R.H.S. Yellow-Green 144A to 145B. Ripe fruit pale yellowish green and glaucous, R.H.S. Yellow-Green 152D. Skin speckled with closely spaced tiny black dots the size of pin pricks. After the fruit passes its climacteric peak and falls from the tree, brown blotches appear which spread to cover the entire skin surface, as is typical for the species.

*Color break.*—Above noted color change is basically reliable. In addition, in most years, a brown collar develops around the "neck" where the fruit attaches to the peduncle. This color break precedes browning of the skin anywhere else on the fruit and is a reliable sign that the fruit is ready to pick.

*Skin thickness.*—Medium-thick and tough.

*Aril.*—Thin, tender, and edible.

*Fleshiness.*—Very high. Percent seed is 3.3 on average. The average quantity of pulp per seed is 34.8 gm.

*Flesh color.*—Creamy yellow and uniform throughout. Color ranges from R.H.S. Yellow-Orange 21B to 22B.

*Aroma of uncut fruit.*—Pleasant. Low power.

*Aroma of cut fruit.*—Pleasant. Low power.

*Flavor.*—Very sweet, Brix 26%, mild, nonbitter, and nonastrigent. Pungent asiminous component low.

*Aftertaste.*—Pleasant, long lingering, no negative components.

*Consistency.*—Flesh is very firm (very atypical of pawpaw) and very smooth, closely resembling 'Haas' avocado in texture and consistency. Melting in the mouth. Pleasant mouth-feel. No detectable fiber or grit.

*Use.*—Principally for fresh eating as a dessert fruit. Secondarily in processed products.

Seed:

*Size.*—Large. 1.40 gm average weight. Dimensions 24.0 mm long, 14.6 mm wide, 7.1 thick on average.

*Color.*—Dark brown. R.H.S. Brown 200A.

*Number per fruit.*—7 per average fruit of 300 gm. As fruit size varies greatly in pawpaw, the seed number per fruit is not a stable character, unlike the seed-to-fruit ratio (percent seed) which is stable.

Physiological and ecological characters:

*Graftability.*—Very easy to graft by virtually all methods. Percent take is medium to high for pawpaw, in vicinity of 85–95%.

*Habit of tree after grafting.*—Medium vigor. Time to flowering on established rootstock is roughly three years. It appears that common seedling rootstocks have more vigor than the tree's own roots.

*Pruning.*—The tree responds well with moderate vigor to pruning. Flowering and general vigor improved by pruning.

*Flower count.*—Medium to high. Average of 4.5 blossoms per branch on vigorous branches, but flower number varies considerably depending on vigor of the branch.

*Self-fruitfulness.*—Requires cross pollination.

*Bearing.*—Annual and consistent.

*Fruit set.*—Low, less than 15 percent in most years.

*Yields.*—High. From mature trees approximately 30 lbs. of fruit per tree. At orchard densities of 330 trees per acre, this is 10,000 lbs per acre.

*Keeping quality of fruit (normal storage, 24° C.).*—Short. Three days when ripe. Typical for the species.

*Keeping quality of fruit (cold storage, 2° C.).*—Moderate. Three weeks when picked at the proper time of color break.

*Shipping quality of fruit.*—Medium to good if shipped refrigerated with adequate cushioning. Poor otherwise because of the rapid ripening which is typical for pawpaw.

*Resistance to Talponia plummeriana.*—Susceptible.

*Resistance to Eurytides marcellus.*—Susceptible.

*Resistance to pawpaw decline disease.*—Believed to be susceptible.

Variance in botanical details: The pawpaw tree and its fruit described herein will vary due to climate, soils, growing conditions and culture.

I claim:

1. A new and distinct variety of pawpaw tree, obtained as an open-pollinated seedling of BEF-53 (unpatented), substantially as shown and described herein.

* * * * *